United States Patent [19]

Kawasumi et al.

[11] Patent Number: 5,824,267
[45] Date of Patent: Oct. 20, 1998

[54] METALLIC BACTERICIDAL AGENT

[75] Inventors: Shinroku Kawasumi; Michio Yamada; Masatoshi Honma, all of Kanagawa, Japan

[73] Assignee: Kawasumi Laboritories, Inc., Kanagawa, Japan

[21] Appl. No.: 509,102

[22] Filed: Aug. 1, 1995

[30] Foreign Application Priority Data

Aug. 1, 1994 [JP] Japan ..................................... 6/200085

[51] Int. Cl.$^6$ ............................. A61L 2/16; A01N 25/34; A01N 59/16
[52] U.S. Cl. ........................... 422/28; 424/409; 424/411; 424/421; 424/618
[58] Field of Search ............................. 422/28; 424/409, 424/490, 618, 411, 421

[56] References Cited

U.S. PATENT DOCUMENTS

| | | | |
|---|---|---|---|
| 4,849,223 | 7/1989 | Pratt et al. ............................. | 424/409 |
| 4,906,466 | 3/1990 | Edwards et al. ..................... | 424/421 X |
| 5,130,342 | 7/1992 | McAllister et al. ............. | 428/315.5 X |
| 5,180,585 | 1/1993 | Jacobson et al. ................... | 424/421 X |
| 5,213,801 | 5/1993 | Sakuma et al. ......................... | 424/429 |

*Primary Examiner*—Robert J. Warden
*Assistant Examiner*—E. Leigh McKane
*Attorney, Agent, or Firm*—McAulay Fisher Nissen Goldberg & Kiel, LLP

[57] ABSTRACT

Ceramic or base metal particles of a mean diameter of 0.01 to 0.5 $\mu$m having thereon bactericidal metal particles of a mean diameter of 0.0001 to 0.1 $\mu$m (the mean diameter of the bactericidal metal particles is smaller than the mean diameter of the ceramic or base metal particles) are effective to give a bactericidal surface of a plastic article when they are embedded on the surface under the condition that a portion of the particle is exposed over the surface of the plastic article. The above ceramic or base metal particles having the bactericidal metal particles on their surface are also effective to sterilize liquid or solid material.

8 Claims, 1 Drawing Sheet

METALLIC BACTERICIDAL AGENT

FIELD OF THE INVENTION

The present invention relates to an article of plastic material having a bactericidal surface, and further relates to a method for sterilizing liquid or solid material.

BACKGROUND OF THE INVENTION

Recently, infection with MRSA (methicillin resistant *Staphylococcus aureus*) in a number of hospitals has become a serious problem. The MRSA is resistant to almost all of antibiotics. Therefore, metallic bactericidal agents which are non-antibiotic bactericides are paid attention. From ancient times, it has been known that metals and ions of mercury, silver, copper, zinc, and the like show bactericidal action. The bactericidal mechanism of such bactericidal metals differs from that of antibiotics. Accordingly, it is expected and acknowledged that silver and other bactericidal metals are effective to inhibit growth of various microorganisms and these microorganisms never acquire resistance to the bactericidal metals.

Utilization of the bactericidal metals has been studied in the form of a metallic powder (e.g., silver metal powder), a metal substituted zeolite (e.g., silver zeolite, a zeolite having a silver ion which is introduced by replacing a part of an alkali metal ion of zeolite), a silver plated non-woven fabric, a silver-complex compound. Some metallic bactericidal agents have been employed in practice. For instance, a bactericidal metal or its compound is embedded with an exposed surface in a filament for the preparation of clothing for clinical practitioners or patients, in articles of plastic material such as inner walls of refrigerators, tubs of washing machines, a grip portion of ball-point pen, and a handle of bicycle, or a silver metal powder is mixed with sand of sandpit (or sandbox).

It is known that silver (or other bactericidal metals) inhibits growth of microorganisms by one of two mechanisms, that is, by bactericidal action of silver ions released from a silver compound such as a silver zeolite or a silver complex compound and by production of active oxygen on the surface of silver metal in the form of a silver powder or a silver plated article. The former silver zeolite and silver complex compound show high bactericidal activity within a short time of period, but such high bactericidal activity rapidly diminishes when most of silver ions are released from the zeolite and complex compounds. The latter silver metal shows bactericidal activity for a long time of period, but the bactericidal activity per a unit amount is not high. Further, since a silver metal plated on a fiber is easily dropped, clothes made of the silver metal-plated fibers become to show poor bactericidal activity after the clothes are washed several times.

In summary, known metallic bactericidal agents in the form of a silver metal powder, silver zeolite, a silver complex compound, a plated silver layer, etc., have problems such as expensiveness, unsatisfactory bactericidal activity, and insufficient durability of bactericidal activity.

SUMMARY OF THE INVENTION

The present invention has an object to provide a metallic bactericidal agent which is inexpensive and shows non-toxicity, high bactericidal activity and satisfactory durability of such high bactericidal activity.

There is provided by the invention an article of plastic material having a bactericidal surface in which a number of ceramic or base metal particles of a mean diameter of 0.01 to 0.5 $\mu$m are embedded under the condition that a portion of each particle is exposed over the surface, said ceramic or base metal particles having bactericidal metal particles of a mean diameter of 0.0001 to 0.1 $\mu$m dispersively fixed thereon, the mean diameter of the bactericidal metal particles being smaller than the mean diameter of the ceramic or base metal particles.

Also provided by the invention is a method for sterilizing liquid or solid material, which comprises bringing the liquid or solid material into contact with a number of ceramic or base metal particles of a mean diameter of 0.01 to 0.5 $\mu$m on which bactericidal metal particles of a mean diameter of 0.0001 to 0.1 $\mu$m are dispersively fixed, the mean diameter of the bactericidal metal particles being smaller than the mean diameter of the ceramic or base metal particles.

Preferred embodiments of the present invention are described below:

The ceramic or base metal particles have a mean specific surface of 10 to 100 $m^2/g$.

The bactericidal metal is silver.

The ceramic or base metal particles have a mean diameter of 0.01 to 0.1 $\mu$m.

The bactericidal metal particles are fixed on the ceramic or base metal particles in an amount of 1 to 25 weight %.

The mean diameter of the bactericidal metal partiles is 1 to 20% of the mean diameter of the ceramic or ase metal particles.

DETAILED DESCRIPTION OF THE INVENTION

Figure 1:
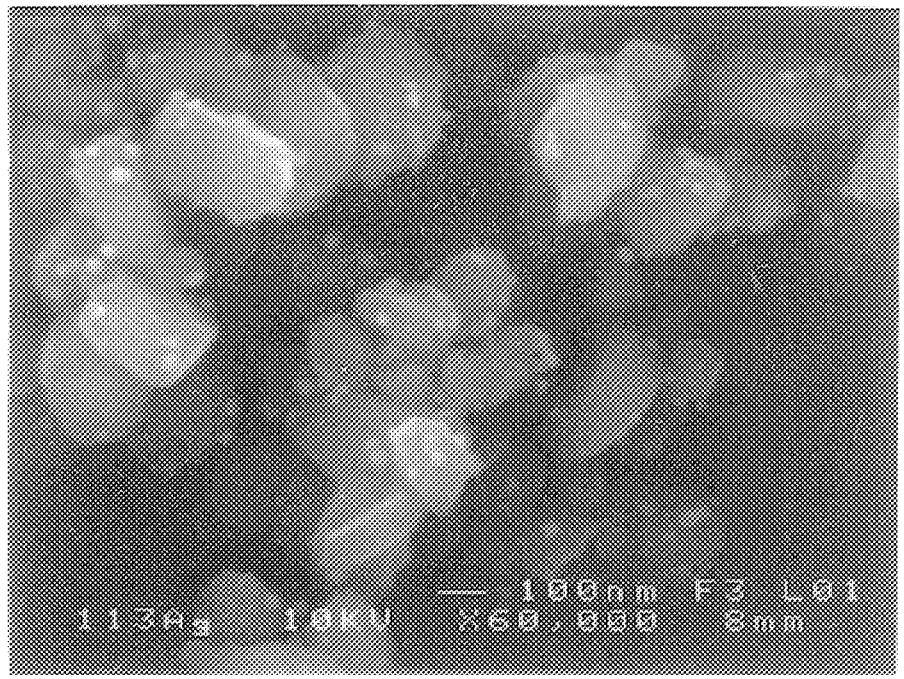
FIG. 1 is a microscopic photograph (magnification: 60,000) of a titanium dioxide powder having silver metal particles on its surface, which is according to the invention.

The present inventors have noted that ceramic fine particles (or fine particles of base metal) such as fine particles of barium titanate, titanium dioxide, and silica show relatively low agglomeration, and these particles can easily receive extremely fine silver metal particles on their surfaces by a chemical deposition method. Further, the inventors have found that the fine ceramic particles having very fine silver metal particles thereon are uniformly dispersed in a plastic resin material for molding, and when such ceramic particles having the silver metal micro-particles are embedded in a molded material in such manner that a portion of each ceramic particle is exposed over the surface of the molded material, the molded material show high and durable bactericidal activity. The present invention has been made on this inventor's finding.

The generally employed silver metal fine powder has a mean particle diameter of several microns (e.g., 1 to 10 $\mu$m). A silver metal powder having more small particle diameter shows extremely high agglomeration so as to produce a secondary and more agglomerated mass. Moreover, such agglomerated mass is highly resistant to dispersion (i.e., deagglomeration) to give the original primary particles. In contrast, the extremely fine silver metal particles (such as those having a very small diameter of less than 0.1 $\mu$m) deposited on the ceramic or base metal fine powder show relatively low agglomeration and can be uniformly dispersed in a resin material or the like together with the ceramic or base metal carrier particles.

As is described above, the metallic bactericidal agent of the invention which comprises a fine ceramic or base metal powder having extremely fine silver metal particles on its surface is well compatible with a resin material. Therefore, the resin material having the ceramic or base metal powder therein shows stable resin characteristics such as fluidity and is almost free from deterioration possibly caused by incorporation of additives. Moreover, since the metallic bactericidal agent of the invention is highly heat resistant (for instance, a titanium dioxide powder having a silver metal fine particles thereon does not deteriorate even at 350° C.), the bactericidal agent does not show decrease of its bactericidal activity after it is kneaded with a melted resin material under heating. It is further noted that a resin material containing the metallic bactericidal agent of the invention shows almost no variation in its resistance to ultra-violet rays, resistance to weather, resistance to chemicals, surface gloss, and physical strength. Accordingly, the metallic bactericidal agent of the invention is freely employable taking almost no consideration of adverse effect to resin materials.

Examples of the micro-powdery ceramic or base metal material which forms a core or carrier of the metallic bactericidal agent of the invention include barium titanate, titanium dioxide, silica (silicone dioxide), alumina (aluminum oxide), zirconium oxide, nickel metal, and copper metal (for depositing silver fine particles thereon). Preferred are ceramic powders such as barium titanate powder, titanium dioxide powder, and silica.

The ceramic or base metal particles have a mean diameter of 0.01 to 0.5 $\mu$m (preferably, not larger than 0.1 $\mu$m; more preferably, not larger than 0.08 $\mu$m). Moreover, the ceramic or base metal particles preferably have a large specific surface area in the range of 5 to 100 m$^2$/g, more preferably 10 to 100 m$^2$/g.

The metallic bactericidal agent of the invention is prepared by dispersively depositing a silver or other bactericidal metal in the form of an extremely fine particles by known chemical deposition methods. In more detail, the ceramic or base metal powder is dispersed in an aqueous medium, and mixed with an aqueous solution of a salt of silver or other bactericidal metal. To the resulting dispersion is added a reducing agent so as to deposit micro-fine particles of silver or other bactericidal metal over the surface of the ceramic or base metal powder.

A number of bactericidal metals are known. Silver is preferred because it is highly safe and shows high bactericidal activity. However, other bactericidal metals such as copper and zinc can be employed depending on purposes.

The ratio of the core material (i.e., ceramic or base metal powder) and the bactericidal metal dispersed thereon preferably ranges 100:0.1 to 100:60, preferably 100:1 to 100:25, by weight. The preferred ratio can be described by 70:20 to 99:1, preferably 66:34 to 95:5, by weight, in terms of the core material:bactericidal metal.

The fine powdery metallic bactericidal agent of the invention can be incorporated in a variety of molded articles under the condition that a portion of each particle is exposed over the surface of the molded articles, and gives semipermanent bactericidal activity. Examples of the articles include filament and fiber of synthetic polymers (such as polyester, polyamide, and polyethylene). The filament or fiber having the fine powder metallic bactericidal agent under the condition a portion of each particle is embedded and other portion is exposed over its surface can be woven or knitted to give clothing for medical practitioners and patients, sheets for hospital beds, curtains for hospitals, or bandages. The above filament or fiber can be also used for preparing underwear and socks. The fine powdery metallic bactericidal agent of the invention can be kneaded with resin materials for producing inner walls of refrigerators, various parts to be equipped within refrigerators, washing tubs of washing machines, filters of vacuum cleaners, grips of ball-point pens, various parts to be installed within motor cars, receivers of telephones, tableware, bactericidal paints, keyboards of personal computers, wall papers, filters and various parts for water purifiers, plastic kitchen boards, caulking material, fishing nets, wrapping films for meat, fish and vegetable, and flower vases. The fine powdery metallic bactericidal agent of the invention can be mixed with sand in a sand pit to sterilize the sand, or can be incorporated into water within a flower vase so as to sterilize the water and prolong the life of flower. The fine powdery metallic bactericidal agent of the invention can be mixed with a deodorant powder or a nursery powder to inhibit growth of microorganisms on the skin.

EXAMPLE 1

Silver-Deposited Titanium Dioxide Powder

1) Preparation of silver diamine nitrate solution

In 200 mL of pure water was dissolved 8.0 g of silver nitrate (containing 5.0 g of Ag). To this solution was added 50 mL of aqueous ammonia to give an aqueous solution of an ammine complex of silver nitrate (silver diamine nitrate).

2) Preparation of silver(10 wt. %)-deposited titanium dioxide powder

The silver diamine nitrate solution obtained 1) above and 1,000 mL of pure water were added to 45 g of a powdery titanium dioxide (mean particle diameter: 0.02 $\mu$m, specific surface area: 40.8 m$^2$/g), and the mixture was processed by a ultra-sonic dispersion mixer. To the resulting dispersion was added 200 mL of an aqueous glucose solution containing 10 g of glucose. The mixture was then stirred at 40°–60° C. for 1 hour to deposit metallic silver micro fine particles on the titanium dioxide powder. The silver-deposited powder was collected by decantation, washed with water and dried to give 50 g of a silver(10 wt. %)-deposited titanium dioxide powder (mean particle diameter: 0.02 $\mu$m, specific surface area: 40.6 m$^2$/g).

EXAMPLE 2

Silver-Deposited Titanium Dioxide Powder

1) Preparation of silver diamine nitrate solution

In 1,000 mL of pure water was dissolved 40 g of silver nitrate (containing 25 g of Ag). To this solution was added 250 mL of aqueous ammonia to give an aqueous solution of an ammine complex of silver nitrate (silver diamine nitrate).

2) Preparation of silver(50 wt. %)-deposited titanium dioxide powder

The silver diamine nitrate solution obtained 1) above was added to 25 g of a powdery titanium dioxide (mean particle diameter: 0.02 $\mu$m, specific surface area: 40.8 m$^2$/g), and the mixture was processed by a ultra-sonic dispersion mixer. To the resulting dispersion was added 500 mL of an aqueous glucose solution containing 50 g of glucose. The mixture was then stirred at 40°–60° C. for 1 hour to deposit metallic silver micro fine particles on the titanium dioxide powder. The silver-deposited powder was collected by decantation, washed with water and dried to give 50 g of a silver(50 wt. %)-deposited titanium dioxide powder (mean particle diameter: 0.04 $\mu$m, specific surface area: 24.6 m$^2$/g).

EXAMPLE 3

Silver-Deposited Titanium Dioxide Powder

1) Preparation of silver diamine nitrate solution

In 90 mL of pure water was dissolved 4.0 g of silver nitrate (containing 2.5 g of Ag). To this solution was added 10 mL of aqueous ammonia to give an aqueous solution of an ammine complex of silver nitrate (silver diamine nitrate).

2) Preparation of silver(5 wt. %)-deposited titanium dioxide powder

The silver diamine nitrate solution obtained 1) above and 250 mL of pure water were added to 47.5 g of a powdery titanium dioxide (mean particle diameter: 0.2 μm, specific surface area: 11.43 m$^2$/g), and the mixture was processed by a ultra-sonic dispersion mixer. To the resulting dispersion was added 50 mL of an aqueous glucose solution containing 5 g of glucose. The mixture was then stirred at 40°–60° C. for 1 hour to deposit metallic silver micro fine particles on the titanium dioxide powder. The silver-deposited powder was collected by decantation, washed with water and dried to give 50 g of a silver(5 wt. %)-deposited titanium dioxide powder (mean particle diameter: 0.2 μm, specific surface area: 10.6 m$^2$/g).

A microscopic photograph (magnification: 60,000) of the resulting silver-deposited titanium dioxide powder is given in FIG. 1. It is observed that micro fine particles of silver metal are dispersively deposited on the surface of the titanium dioxide fine powder.

EXAMPLE 4

Silver-Deposited Titanium Dioxide Powder

1) Preparation of silver diamine nitrate solution

In 80 mL of pure water was dissolved 8.0 g of silver nitrate (containing 5.0 g of Ag). To this solution was added 20 mL of aqueous ammonia to give an aqueous solution of an ammine complex of silver nitrate (silver diamine nitrate).

2) Preparation of silver(10 wt. %)-deposited titanium dioxide powder

In the silver diamine nitrate solution obtained 1) above was dispersed 45 g of a powdery titanium dioxide (mean particle diameter: 0.2 μm, specific surface area: 11.43 m$^2$/g), and the mixture was processed by a ultrasonic dispersion mixer. To the resulting dispersion was added 100 mL of an aqueous glucose solution containing 10 g of glucose. The mixture was then stirred at 40°–60° C. for 1 hour to deposit metallic silver micro fine particles on the titanium dioxide powder. The silver-deposited powder was collected by decantation, washed with water and dried to give 50 g of a silver(10 wt. %)-deposited titanium dioxide powder (mean particle diameter: 0.2 μm, specific surface area: 9.85 m$^2$/g).

EXAMPLE 5

Silver-Deposited Titanium Dioxide Powder

1) Preparation of silver diamine nitrate solution

In 48 mL of pure water was dissolved 0.8 g of silver nitrate (containing 0.5 g of Ag). To this solution was added 2 mL of aqueous ammonia to give an aqueous solution of an ammine complex of silver nitrate (silver diamine nitrate).

2) Preparation of silver(1 wt. %)-deposited titanium dioxide powder

In the silver diamine nitrate solution obtained 1) above was dispersed 49.5 g of a powdery titanium dioxide (mean particle diameter: 0.2 μm, specific surface area: 11.43 m$^2$/g), and the mixture was processed by a ultrasonic dispersion mixer. To the resulting dispersion was added 10 mL of an aqueous glucose solution containing 1 g of glucose. The mixture was then stirred at 40°–60° C. for 1 hour to deposit metallic silver micro fine particles on the titanium dioxide powder. The silver-deposited powder was collected by decantation, washed with water and dried to give 50 g of a silver (1 wt. %) -deposited titanium dioxide powder (mean particle diameter: 0.2 μm, specific surface area: 10.42 m$^2$/g).

EXAMPLE 6

Evaluation of Bactericidal Activity

Bactericidal activity against *Escherichia coli* was examined using the silver metal-deposited titanium dioxide powders of Examples 1 and 2 as well as a silver metal powder (mean particle diameter: 1 μm, specific surface area: 0.4 m$^2$/g: control) using the conventional method. It was observed that the bactericidal activity given by the silver-deposited titanium dioxide powder was apparently higher than the bactericidal activity of the control silver metal powder.

EXAMPLE 7

Evaluation of Bactericidal Activity

Bactericidal activities against MRSA (methicillin resistant *Staphylococcus aureus*), *Escherichia coli*, and *Pseudomonas aeruginosa* were evaluated using the silver deposited titanium dioxide powders of Examples 3 and 5 (amount of deposited silver metal: 5 wt. % for the powder of Example 3 and 1 wt. % for the powder of Example 5). For the evaluation, 50 mM phosphate buffers of different concentrations (100 μg/mL to 0.20 μg/mL) and a commercially available broth (produced by Nissui Co., Ltd.) were used, and incubation was conducted at 35° C. for 18 hours. The bactericidal activity was evaluated by examining increase or decrease of the cultured microorganisms. The results are set forth in Table 1. The control experiments were also conducted using the phosphate buffer which did not contain the silver metal-deposited titanium dioxide powder. In consideration of increase of the cultured microorganisms in the control experiment (number of incubated microorganisms: 10,000; number of cultured microorganisms: 100,000), the effective amount of bactericidal agent was determined when the number of microorganisms decreased to 50 or less.

TABLE 1

| Ag—TiO$_2$ Powder | MRSA | E. coli | P. aeruginosa |
|---|---|---|---|
| Example 3 (Ag: 5%) | 0.78 | 0.20 | 3.13 |
| Example 5 (Ag: 1%) | 1.56 | 0.20 | 6.25 |

EXAMPLE 8

Preparation of Bactericidal Article

One weight part of the silver-deposited titanium dioxide powder obtained in Example 1 was mixed with 100 weight parts of ABS resin. The mixture was kneaded and molded to prepare a ABS resin film sheet. Microscopic observation on the resin film sheet revealed that a large number of the silver-deposited titanium dioxide particles were embedded in the sheet under the condition that a portion of the embedded particle was exposed over the surface of the sheet.

EXAMPLE 9

Preparation of Bactericidal Article

One weight part of the silver-deposited titanium dioxide powder obtained in Example 3 was mixed with 100 weight parts of a polyethylene resin. The mixture was kneaded and molded to prepare a polyethylene resin film sheet of 20 μm thick. Microscopic observation on the resin film sheet revealed that a large number of the silver-deposited titanium dioxide particles were embedded in the sheet under the condition that a portion of the embedded particle was exposed over the surface of the sheet.

A piece of uncooked fish (*Bdryx splendens*) was wrapped with the above film sheet having the partly embedded silver-deposited titanium oxide powder and kept at room temperature. In parallel, a similar piece of the uncooked fish was wrapped with a simple polyethylene resin film of 20 μm thick and kept at room temperature. After 16 days, the color of the fish piece of the control trial darkened, while the fish piece wrapped with the polyethylene resin sheet containing the Ag-deposited $TiO_2$ showed no color change.

EXAMPLE 10

Preparation of Bactericidal Article

One weight part of the silver-deposited titanium dioxide powder obtained in Example 3 was mixed with 100 weight parts of a polyethylene resin. The mixture was kneaded and molded to prepare a polyethylene resin filament of 300 μm thick. Microscopic observation on the resin filament revealed that a large number of the silver-deposited titanium dioxide particles were embedded in the filament and slightly protruded from the surface of the filament.

In a flower vase, 300 mL of water and 30 cm (0.02 g) of the above-obtained filament. In the vase, a tulip was placed and kept at room temperature. A control experiment was conducted in parallel using water alone. After 10 days, the tulip of the control experiment drooped and its color darkened, while the tulip kept in water in the presence of the polyethylene resin filament containing the Ag-deposited $TiO_2$ showed almost no change.

We claim:

1. A method for sterilizing liquid or solid materials, which comprises bringing the liquid or solid material into contact with a number of bactericidal particles consisting essentially of ceramic or base metal particles of a mean diameter of 0.01 to 0.5 μm and silver metal particles of a mean diameter of 0.0001 to 0.1 μm dispersively fixed on the ceramic or base metal particle, the mean diameter of the silver metal particles being 1 to 20% of the mean diameter of the ceramic or base metal particles.

2. The method of claim 1, wherein the ceramic or base metal particles have a mean specific surface of 5 to 100 $m^2/g$.

3. The method of claim 1, wherein the bactericidal metal particles are fixed on the ceramic or base metal particles in an amount of 1 to 25 weight %.

4. An article comprising a plastic material having a bactericidal surface in which a number of bactericidal particles are embedded under the condition that portion of each bactericidal particle is exposed over the surface, said bactericidal particle consisting essentially of a ceramic or base metal particle of a mean diameter of 0.01 to 0.5 μm and silver metal particles of a mean diameter of 0.0001 to 0.1 μm dispersively fixed on the ceramic or base metal particle, the mean diameter of the silver metal particle being 1 to 20% of the mean diameter of the ceramic or base metal particle.

5. The article of claim 4, wherein the ceramic or base metal particles have a mean specific surface of 5 to 100 $m^2/g$.

6. The article of claim 4, wherein the ceramic or base metal particles have a mean specific surface of 10 to 100 $m^2/g$.

7. The article of claim 4, wherein the ceramic or base metal particles have a mean diameter of 0.01 to 0.1 μm.

8. The article of claim 4, wherein the bactericidal metal particles are fixed on the ceramic or base metal particles in an amount of 1 to 25 weight %.

\* \* \* \* \*